United States Patent [19]

Wang

[11] Patent Number: 5,522,801
[45] Date of Patent: Jun. 4, 1996

[54] INTEGRATE-FORMING SILICONE BALLOON CATHETER

[76] Inventor: Abe Wang, 7340 McMath Road, Richmond, B.C., Canada, V6Y 1B7

[21] Appl. No.: 374,299

[22] Filed: Jan. 18, 1995

[51] Int. Cl.⁶ .................................................. A61M 29/00
[52] U.S. Cl. ............................ 604/96; 604/103; 606/192; 606/194
[58] Field of Search ...................... 604/96–103; 606/191, 606/192, 194

[56] References Cited

U.S. PATENT DOCUMENTS

| | | | |
|---|---|---|---|
| 2,690,595 | 10/1954 | Raiche | 604/96 |
| 2,862,497 | 12/1958 | Ragano | 604/96 |
| 3,053,257 | 9/1962 | Birtwell | 604/97 |
| 3,394,705 | 7/1968 | Abramson | 604/96 |
| 5,417,657 | 5/1995 | Hauer | 604/96 |

*Primary Examiner*—Corrine M. Maglione
*Assistant Examiner*—Michael L. Arness
*Attorney, Agent, or Firm*—Bacon & Thomas

[57] ABSTRACT

An integrate-forming silicone balloon catheter suitable for use as a urethral catheter, endotracheal tube, gastrostomy tube, nephrostomy catheter, hematuria catheter, etc. The catheter including a shaft, which defines a drainage lumen and has a longitudinal groove on the outside, a conical tip connected to one end of the shaft, a sheath mounted around the shaft and bonded with the shaft together and disposed in flush with the conical tip, the sheath having a inflatable section without enlarged step and not bonded to the shaft for inflating a balloon, the balloon defining with the shaft a space communicated with the longitudinal groove into which space a solution can be filled to inflate the balloon.

2 Claims, 8 Drawing Sheets

INTEGRATE-FORMING SILICONE BALLOON CATHETER

BACKGROUND OF THE INVENTION

The present invention relates to medical catheters, and relates more particularly to an integrate-forming silicone formed of an even outside diameter balloon catheter which comprises a shaft having a conical tip, and a sheath made around the shaft and disposed in flush with the conical tip. The sheath has an inflatable section which forms into a balloon that can be inflated to hold down the catheter in position when the catheter is inserted into an organ of the patient's body and deflated to an original even outside diameter after using for a painless in-out operation.

For example, if a patient cannot discharge urine because of a certain disease, an instrument such as a urethral catheter must be used and inserted through the urethral into the urinary bladder to carry urine away from the urinary bladder. In order to hold down the urethral catheter in the urinary bladder, a positioning means is required. FIGS. 1 through 3C–3C show a urethral catheter according to the prior art. The urethral catheter comprises a shaft with a balloon 10, having one end terminating in a plug segment 11 and an opposite end terminating in a three-way drain unit 12, which comprises an intermediate drainage and irrigation hole 22, and a bifurcated funnel 23 and 29. The bifurcated funnel has one end fitted with a valve for balloon inflation and the other end for medicine administration. The drainage and irrigation hole 22 is for urine drainage and irrigation shaft. One branch tube 23 is connected to an inflation lumen 24, which is disposed within the shaft 10. The inflation lumen 24 has an opposite end connected to a valve 19 in the plug segment 11. The plug segment 11 is connected with a conical tip 11'. A balloon 27 is mounted around the shaft 10. The inflation lumen 24 has an outlet communicated with the inside space of the balloon 27. When the urethral catheter is inserted through the urethra into the urinary bladder, a solution can be filled through the branch tube 23 and the inflation lumen 24 to the balloon 27, causing the balloon 27 inflated and stopped against the inside wall of the urethra, and therefore the tip of the urethral catheter is maintained in position for guiding urine out of the urinary bladder. This structure of urethral catheter is complicated to manufacture because the balloon 27 is separately made and then bonded to the shaft. Before the installation of the balloon 27, the shaft 10 must be drilled with a through hole to impart a passage between failure will occur. Because the balloon is bonded to the shaft 10, an enlarged step is formed in the connecting area between the balloon and the shaft. This enlarged step will rub against the inside wall of the urethra to cause pain when the urethral catheter is inseted into the urethra. Furthermore, the complicated manufacturing process of this structure of urethral catheter greatly increases the manufacturing time and cost.

Figure 1:
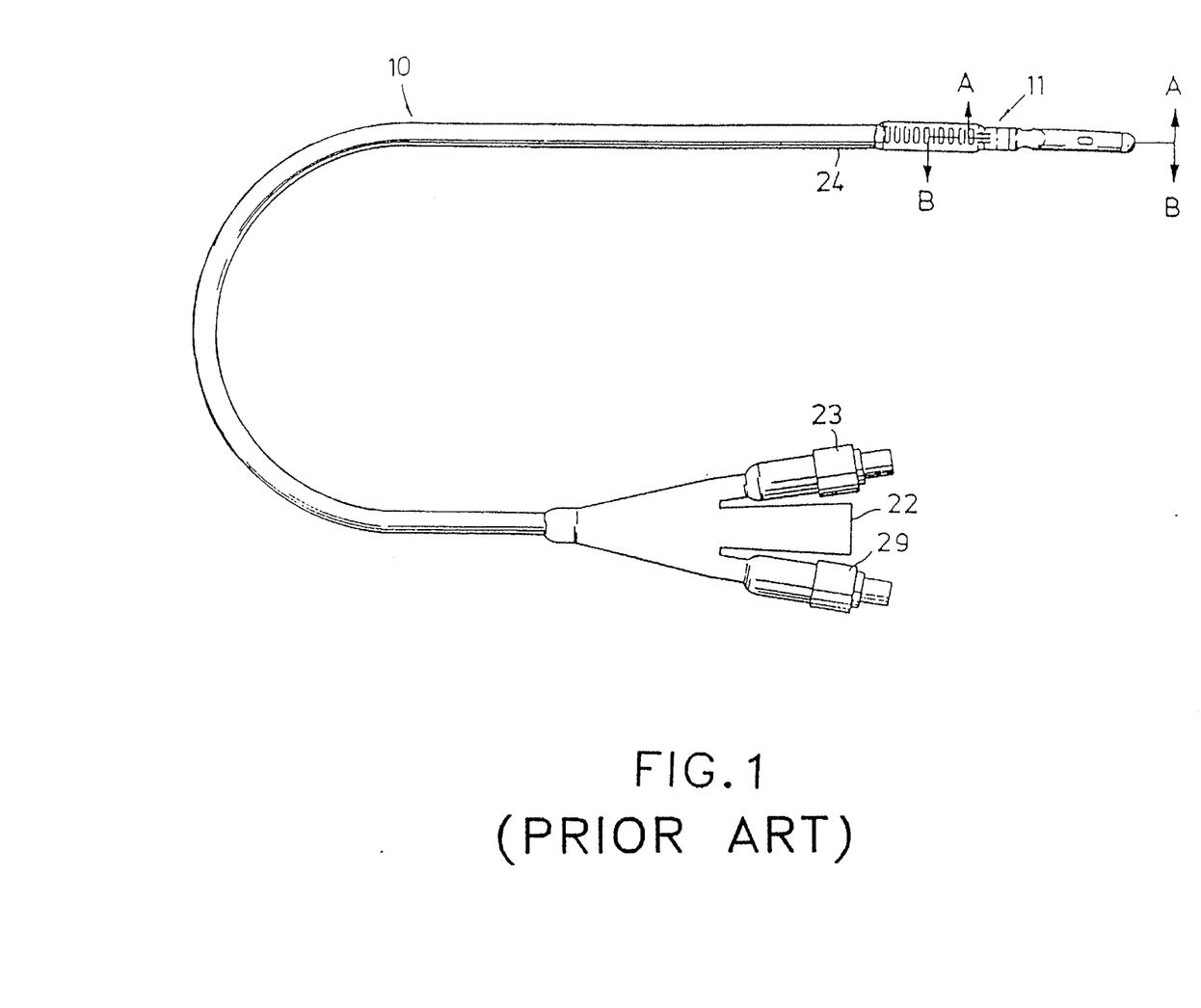
FIGS. 1, 2 & 3 show a balloon catheter according to a conventional prior art.
Figure 2:
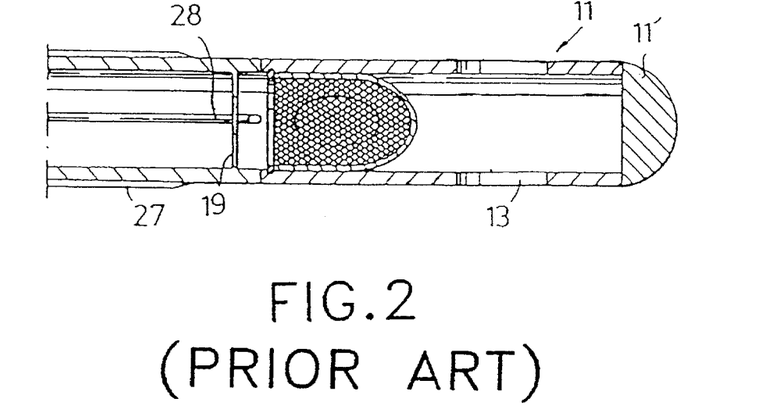
Figure 3:
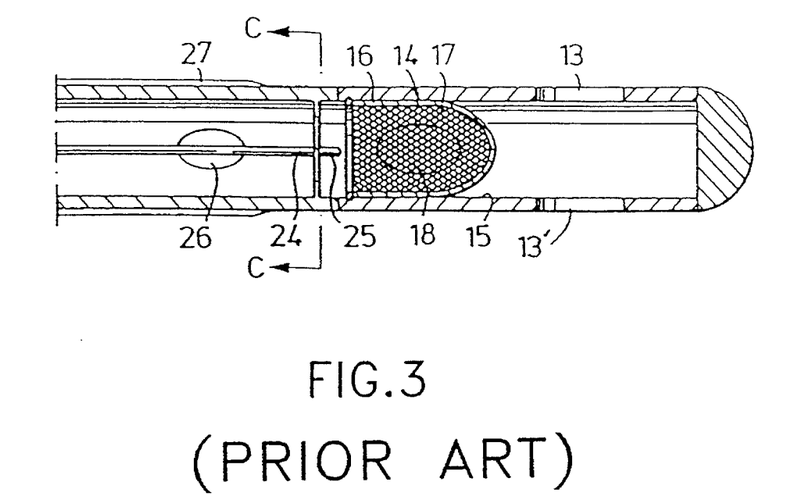
Figure 3C:
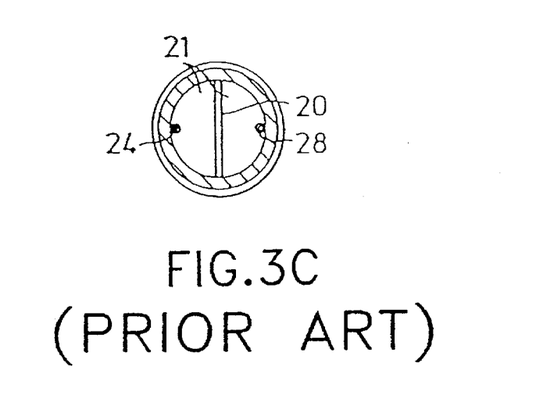
Figure 4:
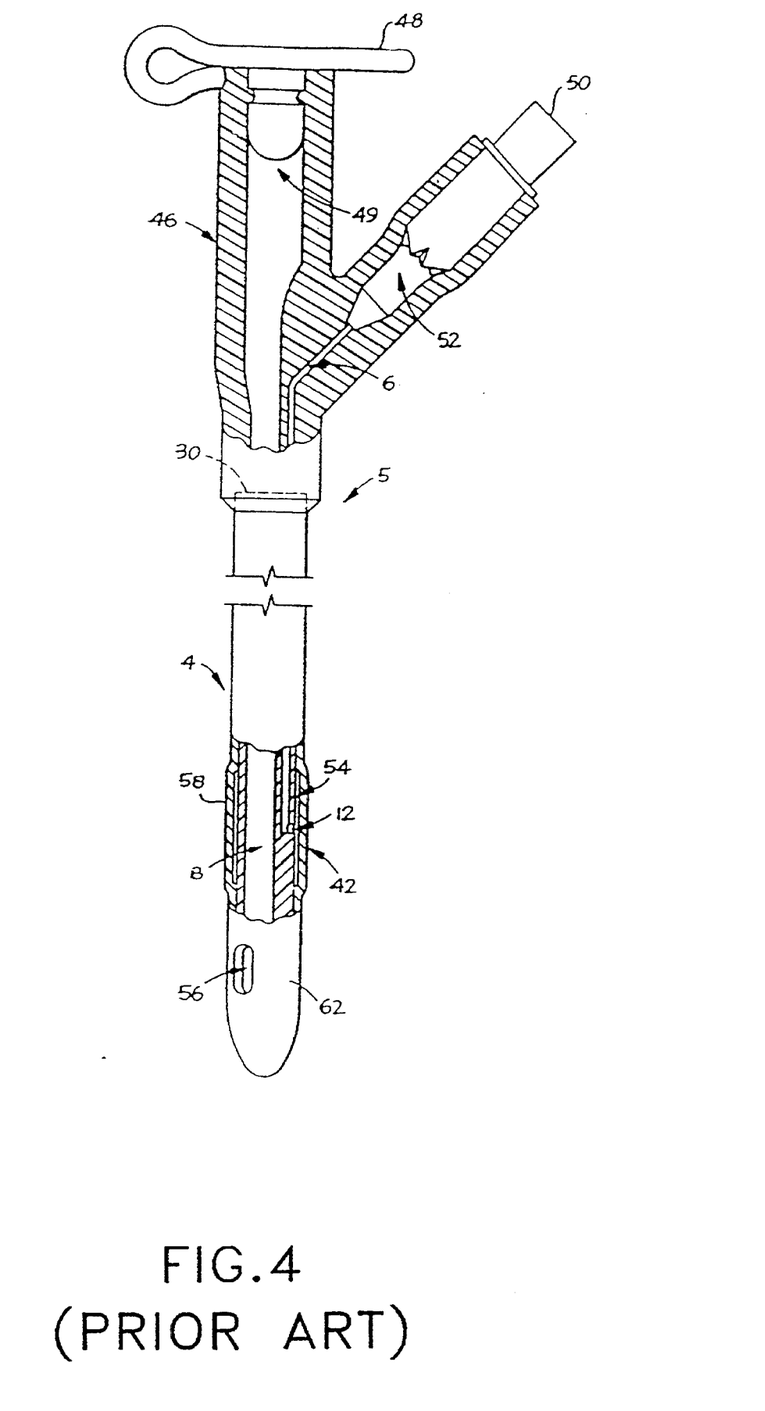
FIG. 4 is transverse schematic view of a Foley catheter made in accordance with U.S. Pat. No. 5,137,671 (original FIG. 15)

U.S. Pat. No. 5,137,671 (see FIG. 4) discloses a method of making a balloon catheter. This method includes the steps of providing a tube having an outer surface and a plurality of lumens including first and second lumens, the tube including a first lumen access-opening in the outer surface communicating with the first lumen; simultaneously coating a first portion of the outer surface with an amount of a bond preventing agent effective to prevent bonding to the first portion of the outer surface and plugging the first lumen access opening; and subsequently coating a second portion of the outer surface and the coating of bond preventing agent on the first portion of the outer surface with a polymetric bonding composition, wherein a resilient overcoat layer is created which is fixed to and integral with the tube proximate the second portion of the outer surface and free from adherence to the tube proximate overcoat layer is created which is fixed to and integral with the tube proximate the second portion of the outer surface and free from adherence to the tube proximate the first portion of the outer surface. However, a balloon catheter made according to this method still cannot eliminate the aforesaid problem because the balloon portion of the overcoat layer is not disposed in flust with the exterior surface of the shaft of the balloon catheter (see FIG. 4).

SUMMARY OF THE INVENTION

The present invention has been accomplished under the circumstances in view. It is therefore an object of the present invention to provide a balloon catheter which can be smoothly inserted through an organ into the patient's body without giving pain to the patient. It is another object of the present invention to provide a balloon catheter which has an approximately circular drain passage for carrying fluid in or out of the patients body for filling medicine or draining the excreta to the patient's body effectively. It is still another object of the present invention to provide a balloon catheter which has a smooth surface that eliminates the deposition of sediment in fluid. It is still another object of the present invention to provide a balloon catheter which is made in integrity. It is still another object of the present invention to provide a balloon catheter which is easy to manufacture.

According to the present invention, the medical catheter comprises a draft, which defines a drain passage for carrying fluid in or out of the organ of a patient's body and has a longitudinal groove on the outside, a conical tip connected to one end of the shaft for inserting through the urethra into the urinary bladder, a sheath mounted around the shaft and bonded with the shaft together and disposed in flush with the conical tip. The sheath has an inflatable section, namely, the balloon which is form of an even out diameter to the catheter and not bonded to the shaft. The balloon defines with the shaft a space communicated with the longitudinal groove into which space a solution can be filled to inflate the balloon. The shaft and sheath are made from silicone rubber by drawing. The sheath is molded on the shaft by a laminate molding process.

BRIEF DESCRIPTION OF THE DRAWINGS

FIG. 3c—3c is a cross section taken along line C—C of FIG. 3;

FIG. 5A is cross-sectional view taken along line I—I of FIG. 5;

DETAILED DESCRIPTION OF THE PREFERRED EMBODIMENT

An medical catheter in accordance with the present invention is, similar to the conventional urethral catheters, comprised of a shaft having one end with tip and balloon, and the other end with a drainage port and a valve for balloon inflation and irrigation. The catheter body is made from silicone rubber by drawing charaterized that the catheter has an inflatable section formed of an even outside diameter to the catheter body.

Figure 5A:
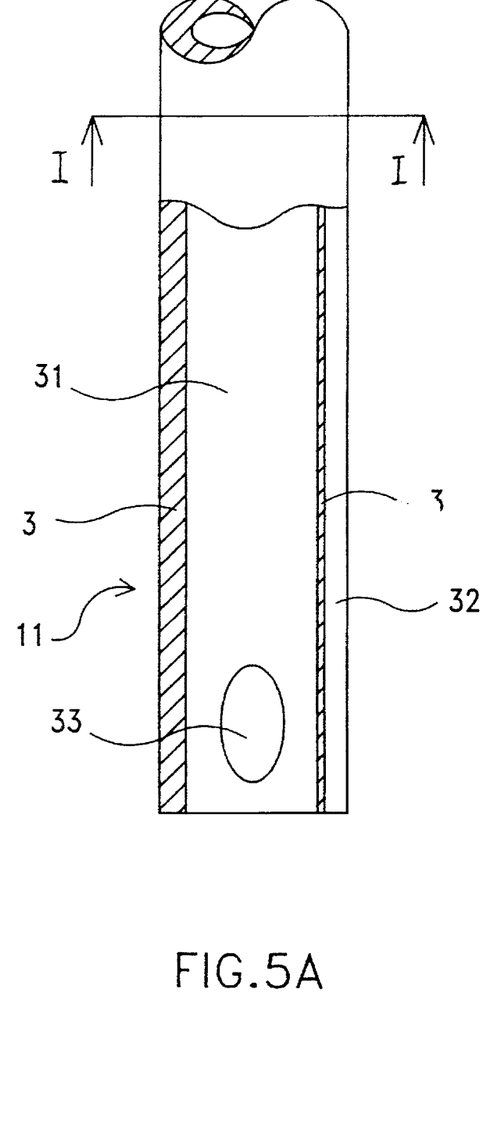
FIG. 5A is a longitudinal view in section of part of the catheter according to a preferable embodiment of the present invention.
Figure 5B:
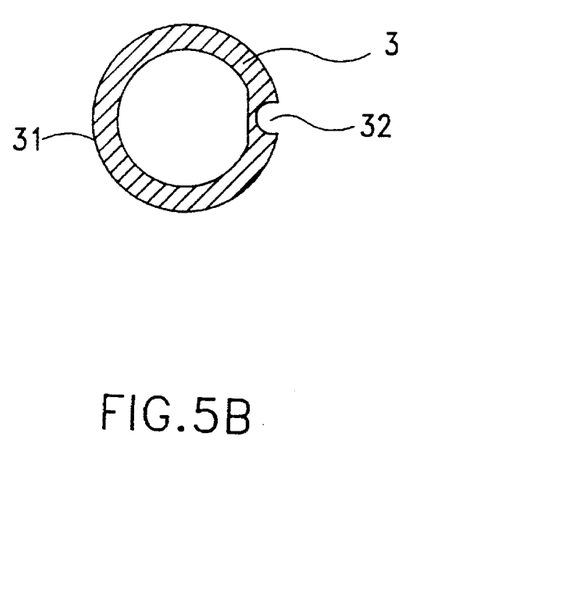

Referring to FIGS. 5 and 5a—5a, the catheter 1 comprises an elongated shaft 3, a longitudinal drain passage 31 defined within the elongated shaft 3, a longitudinal groove 32 longitudinally disposed on the outside of the elongated shaft 3, an opening radially disposed through the elongated shaft 3 near the conical tip 25 for guiding fluid in or out through the passage 31.

Figure 6A:
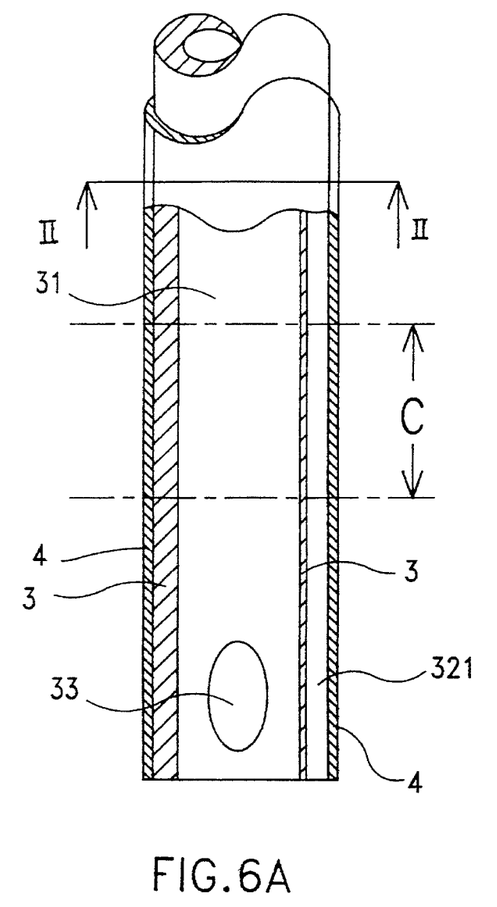
FIG. 6A is a longitudinal view in section of part of the catheter having the sheath coated on and showing an inflatable section C according to the present invention.
Figure 6B:
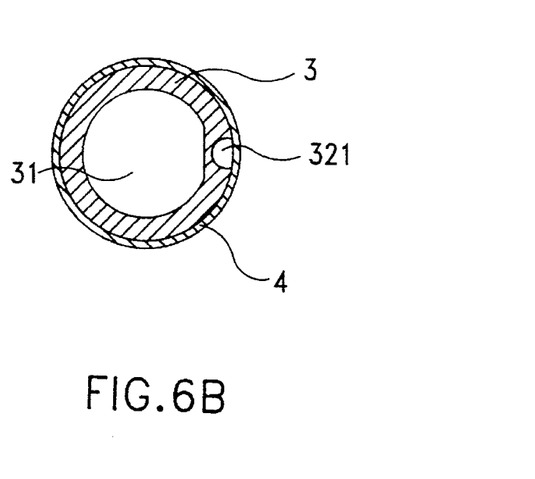
FIG. 6B is a cross section taken along line II—II of FIG. 6.

Referring to FIGS. 6 and 6a—6a, the aforesaid catheter 1 further comprises a sheath 4 mounted around the shaft 3, which has a drain passage 31 on the inside and a longitudinal groove 32 on the outside. When the sheath 4 and the shaft 3 are fastened together, the longitudinal groove 32 is covered by the sheath 4, and therefore the longitudinal groove 32 forms into an inflation and deflation lumen 321. The inside surface of the sheath 4 and the outside surface of shaft 3 are bonded together. A section C diposes to the catheter near the conical tip 25 in a flush manner. Within the section C, the sheath 4 and the shaft 3 are not fastened together for inflating a balloon thereof.

Figure 7:
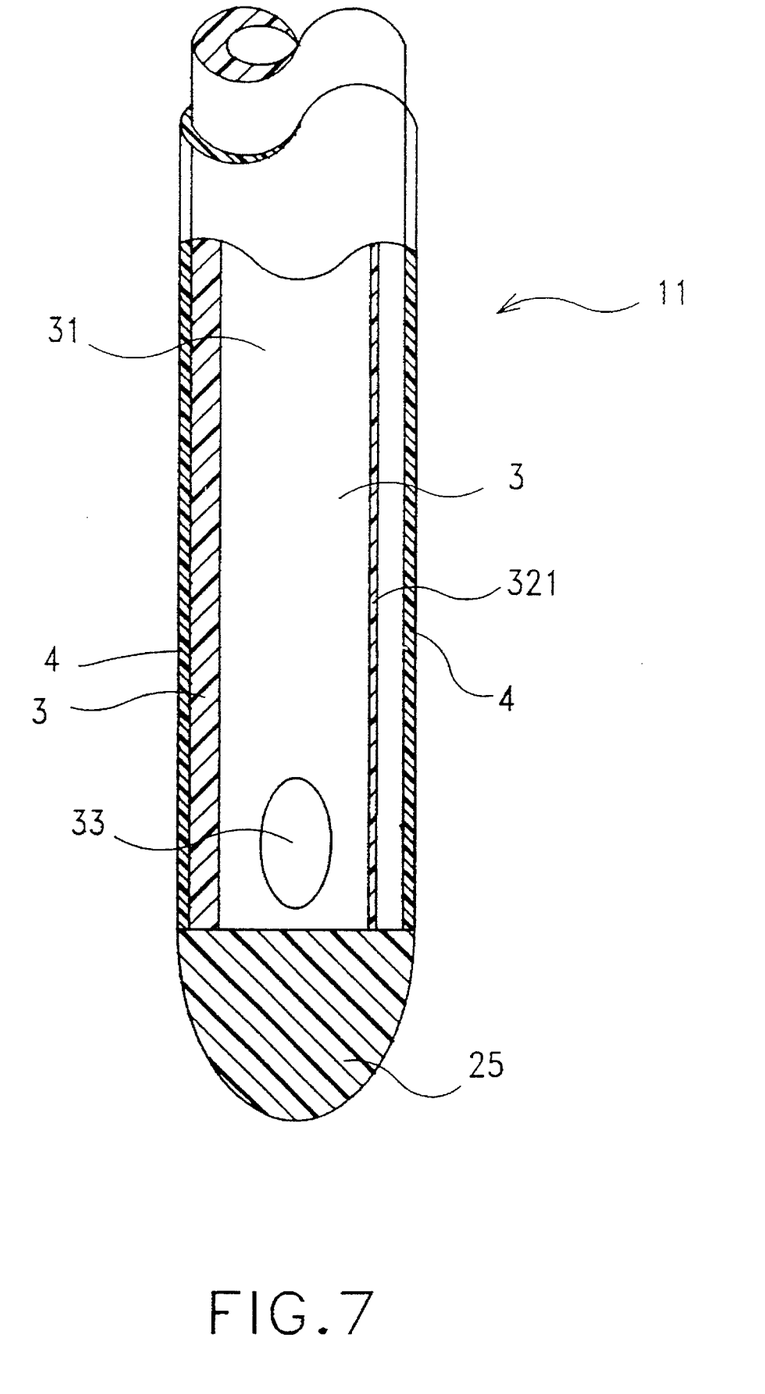
FIG. 7 is similar to FIG. 6 but showing a conical tip connected to the urethral catheter.

Referring to FIG. 7, the conical tip 25 is connected to the end of the shaft 3 and disposed in flush with the sheath 4. Because the outside surface of the conical tip member 25 and the outside surface of the sheath 4 including section C are connected in a flush manner, the tip and section C can be smoothly inserted through the fluid into the organ of patient's body without giving pain to the patient.

Figure 8:
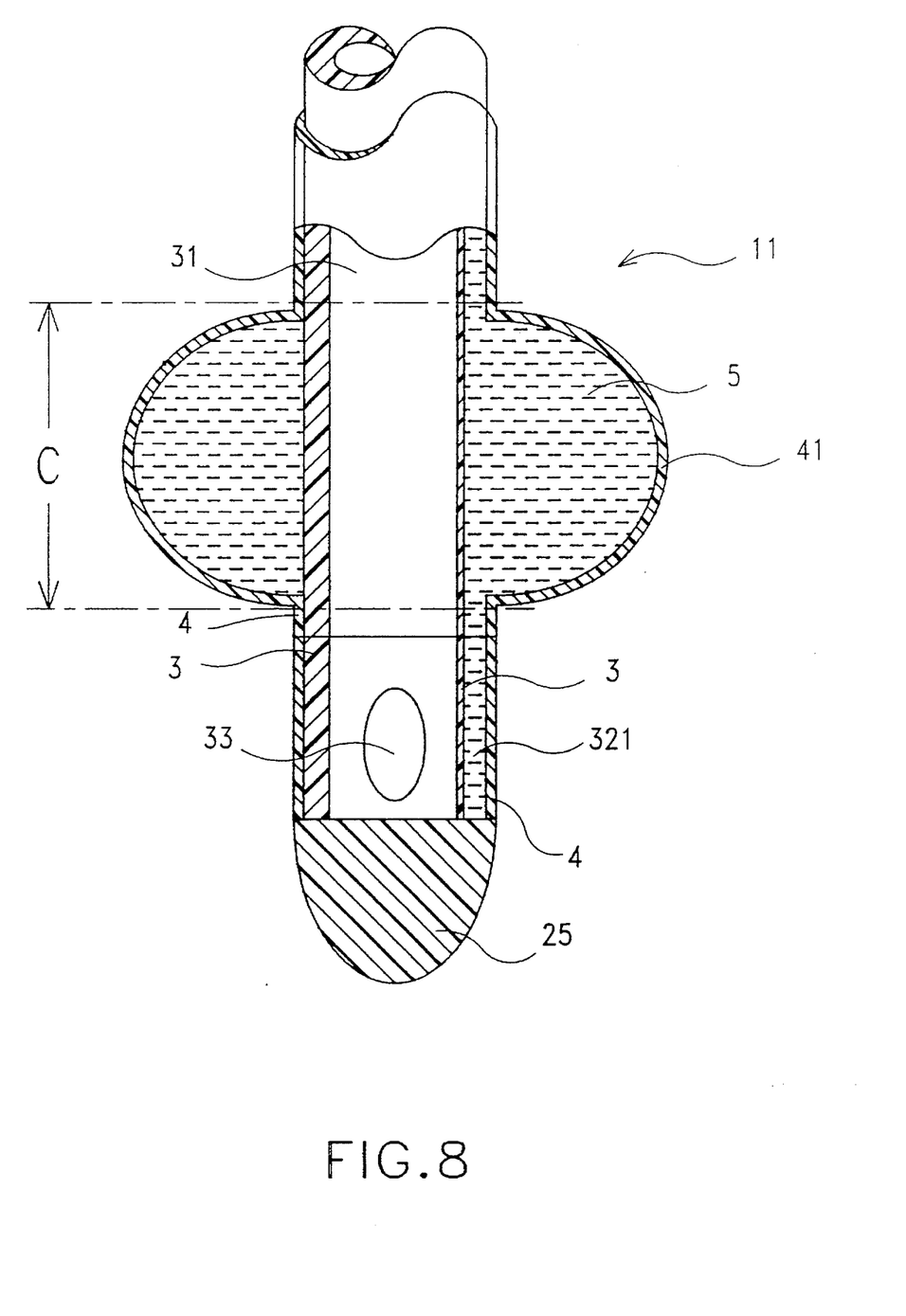
FIG. 8 shows the sheath of the medical catheter of FIG. 6 inflated.

Referring to FIG. 8, when the tip and balloon is inserted through the urethra into the urinary bladder, a solution 5 such as saline or air is injected into the inflation and deflation lumen 321 by a syringe. When the space between the sheath 4 and the shaft 2 within the section C (see also FIG. 6) is filled up with the solution, the sheath 4 of section C is inflated, and therefore an inflated portion, namely, the balloon 41 is formed in section C and stopped against the inside wall of the organ of patient's body to hold down the catheter 1 in the position. After operation, the solution 5 is drawn out of the balloon 41 by the syringe, causing the balloon collapsed, and therefore the catheter 1 can be smoothly removed from the organ of the patient's body.

Figure 9:
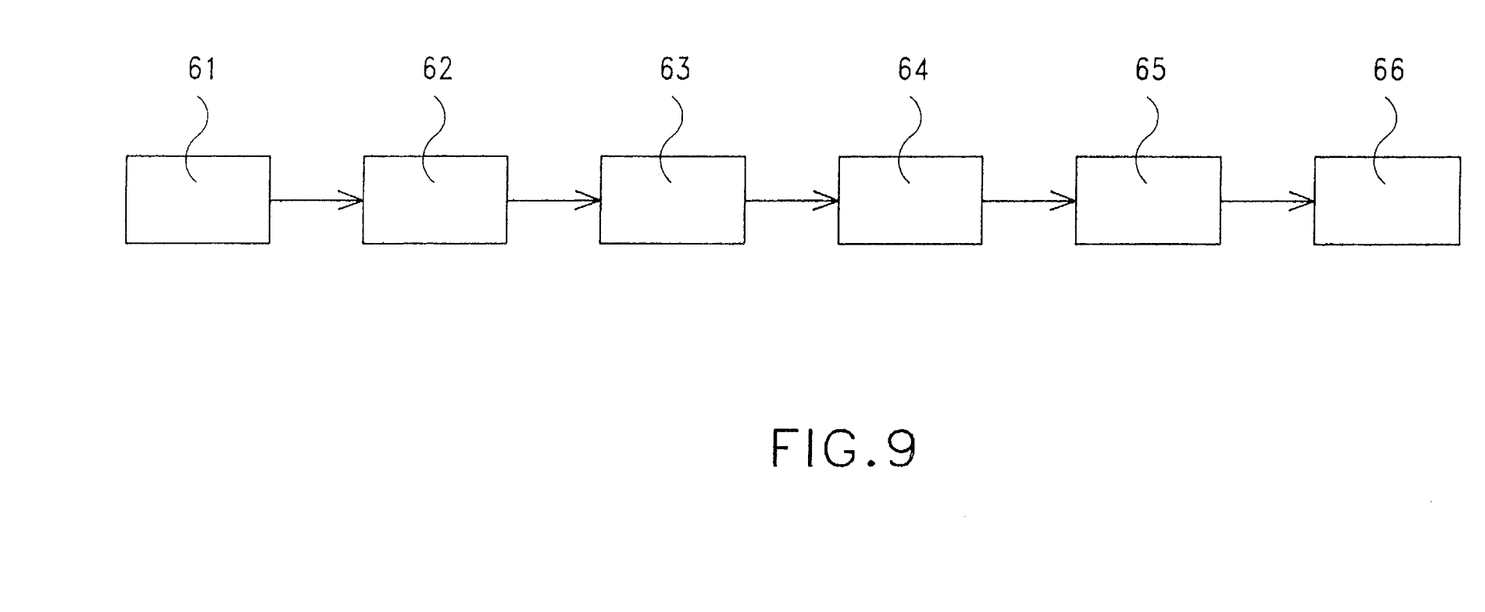
FIG. 9 is a flow chart showing a medical catheter production process according to the present invention.

FIG. 9 is a flow chart showing the production of the medical catheter according to the present invention. The production process includes the steps of:

6: in which silicone rubber is drawn to form a shaft 3 having a drain passage 31 on the inside and a longitudinal groove 32 on the outside (see also FIG. 5);

62: in which the shaft 3 thus obtained from the step 61 is vulcanized;

63: in which a stripping agent is applied to the shaft 3 over the section C (see also FIG. 6);

64: in which a sheath 4 is formed around the tube wall 3 through a laminate molding process (see also FIG. 6);

65: in which the workpiece thus obtained from the step 64 is vulcanized; and

66: in which the vulcanized workpiece is properly cut and then fastened with a conical tip 25.

What is claimed is:

1. A medical catheter comprising: a shaft having an inner surface and an outer surface; a conical tip fixed at one end of the shaft; and a sheath provided around the entire length of the outer surface of the shaft and bonded thereto except a portion of the sheath, wherein the shaft defines a guide lumen bounded by the inner surface for charging a medicine to or discharging human excreta from an organ of a patient's body, the shaft being provided with a longitudinal groove formed in the outer surface on one side thereof and covered by said sheath wherein an outer surface of the whole sheath is disposed flush with the conical tip when there is no fluid introduced into the groove of the shaft, and when a fluid is forcibly introduced into the longitudinal groove of the shaft, the portion of the sheath not bonded to the shaft is inflated radially outwardly to prevent removal of the catheter from the organ.

2. The medical catheter according to claim 1, wherein the portion of the sheath which is not bonded to the shaft is adjacent to the end of the shaft having the conical tip fixed thereto.

\* \* \* \* \*